(12) United States Patent
Meyer et al.

(10) Patent No.: US 8,906,829 B2
(45) Date of Patent: Dec. 9, 2014

(54) SYNERGISTIC ALGICIDAL COMPOSITIONS INCLUDING HYDRAZONE DERIVATIVES AND COPPER

(75) Inventors: Stacy T. Meyer, Zionsville, IN (US); Jeffery D. Webster, New Palestine, IN (US); David H. Young, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/212,675

(22) Filed: Aug. 18, 2011

(65) Prior Publication Data

US 2012/0046170 A1 Feb. 23, 2012

Related U.S. Application Data

(60) Provisional application No. 61/375,471, filed on Aug. 20, 2010.

(51) Int. Cl.
| | | |
|---|---|---|
| *A01N 59/00* | (2006.01) | |
| *A01N 57/02* | (2006.01) | |
| *A01N 57/00* | (2006.01) | |
| *A01N 37/40* | (2006.01) | |
| *A01N 37/28* | (2006.01) | |

(52) U.S. Cl.
CPC ............ *A01N 37/28* (2013.01); *A01N 37/40* (2013.01)
USPC ............ 504/150; 504/151; 504/152; 504/153

(58) Field of Classification Search
None
See application file for complete search history.

(56) References Cited

U.S. PATENT DOCUMENTS

| | | | | |
|---|---|---|---|---|
| 3,163,532 | A * | 12/1964 | Schlesinger | ............... 252/501.1 |
| 4,098,602 | A | 7/1978 | Seymour et al. | |
| 4,547,524 | A | 10/1985 | Kaneko et al. | |
| 2003/0225126 | A1 | 12/2003 | Markham et al. | |
| 2004/0110963 | A1 | 6/2004 | Burri et al. | |

FOREIGN PATENT DOCUMENTS

| | | |
|---|---|---|
| WO | WO 99/62335 A1 | 12/1999 |
| WO | WO 2010/083307 | 7/2010 |

OTHER PUBLICATIONS

International Search Report issued by the USPTO, dated Jan. 6, 2012, for International Application No. PCT/US2011/048260, 2 pages.
International Preliminary Report on Patentability, dated Feb. 26, 2013, for International Application No. PCT/US2011/048260, 5 pages.
Zanobini, A., Supplementary European Search Report for EP App. No. 11818780, Dec. 4, 2013, pp. 1-4.
European Search Opinion for EP App. No. 11818780, Dec. 4, 2013, pp. 1-4.

* cited by examiner

*Primary Examiner* — Alton Pryor
(74) *Attorney, Agent, or Firm* — Faegre Baker Daniels LLP

(57) ABSTRACT

The present invention relates to the use of mixtures containing hydrazone compounds and copper for controlling the growth of algae.

12 Claims, No Drawings

SYNERGISTIC ALGICIDAL COMPOSITIONS INCLUDING HYDRAZONE DERIVATIVES AND COPPER

CROSS REFERENCE TO RELATED APPLICATIONS

This application claims the benefit of U.S. Provisional Patent Application Ser. No. 61/375,471 filed Aug. 20, 2010, which is expressly incorporated by reference herein.

FIELD OF THE INVENTION

The present invention relates to the use of hydrazones in combination with copper, copper-based algicides or other copper-containing materials as synergistic algicidal mixtures.

BACKGROUND

The present invention relates to the use of hydrazone derivatives in combination with copper for controlling algae. In particular, the present invention relates to a method for controlling algae by the use of certain hydrazone derivatives when applied in synergistic mixtures with copper. Such mixtures of hydrazone derivatives with copper are known to exert a synergistic effect towards fungi. Examples include those disclosed in PCT Patent Application PCT/US10/021,040, filed on 14 Jan. 2010.

The presence of algae and other fouling organisms in various aqueous systems or systems exposed to water such as lattices, paints, coatings, cooling water systems, the marine environment, and decorative ponds can cause deterioration or disfigurement of the system. For example, painted surfaces may be disfigured by the unsightly buildup of algae, detracting from the overall aesthetics of the painted article and cooling towers or boats may lose efficiency due to the buildup of algae on surfaces. It is conventional to practice methods which inhibit the algal deterioration of such systems by incorporating a variety of additives or combinations of additives that are characterized by having antialgal activity.

A wide variety of materials have been used to control algae in different environments, including; chlorine/bromine compounds, glutaraldehyde, isothiazoles, organotin formulations, copper salts, quaternary ammonium compounds and triazines. However, each of these materials has deficiencies related to toxicity, pH and temperature sensitivity, limited effectiveness, chemical stability, and/or compatibility. Due to these deficiencies in conventional antialgal compounds, there is a continuing need for more effective antialgal agents.

Copper and copper products are widely used as aquatic biocides and antifouling agents in fresh or marine environments to control unwanted organisms based on the toxicity of copper towards algae, fungi, macrophytes and mollusks (*Handbook of Copper Compounds and Applications*, edited by H. W. Richardson and published by Marcel Dekker, Inc. New York (1997), which is expressly incorporated by reference herein).

Ecological risk assessment studies have shown that copper products, which normally are applied at high use rates, may be toxic to birds, mammals, fish and other aquatic species ("Reregistration Eligibility Decision (RED) for Coppers," EPA 738-R-06-020, July 2006, which is expressly incorporated by reference herein). Thus, while copper is a highly useful agent for controlling the growth of undesirable organisms in different environments, it is desirable to minimize the amount of copper applied.

We have discovered that hydrazone derivatives in combination with copper inhibit the growth of algae. Due to strong synergism between hydrazones and copper, the amount of copper traditionally needed to inhibit growth of algae can be greatly reduced in the presence of hydrazone derivatives. The present invention is a method for controlling algae, comprising applying to the locus of the algae an algicidally effective amount of one or more compounds of the structural formula I in combination with copper.

SUMMARY OF THE INVENTION

One exemplary embodiment of the present disclosure includes a synergistic mixture for controlling the growth of fungi, the synergistic mixture including copper and a hydrazone compound of Formula I:

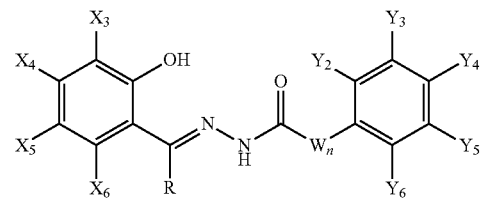

Formula I wherein W is —CHR1-;
n is 0 or 1;
R is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, or $C_3$-$C_6$ halocycloalkyl;
R1 is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl $C_2$-$C_6$ haloalkynyl, $C_3$-$C_6$ halocycloalkyl, substituted aryl, unsubstituted aryl, substituted heteroaryl, or unsubstituted heteroaryl, substituted benzyl, or unsubstituted benzyl;
$X_3$, $X_4$, $X_5$, and $X_6$ are each independently selected from the group consisting of H, halogen, nitro, hydroxyl, cyano, $C_1$-$C_4$ alkyl, $C_1$-$C_4$ alkoxy, $C_2$-$C_4$ alkenyl, $C_2$-$C_4$ alkynyl, $C_1$-$C_4$ alkylthio, $C_1$-$C_4$ haloalkyl, $C_1$-$C_4$ haloalkoxy, $C_2$-$C_4$ haloalkenyl, $C_2$-$C_4$ haloalkynyl, $C_1$-$C_4$ haloalkylthio, —$SO_2$R1, —SONR1R1, —CR1=NOR1, —CONR1R1, —NR1COOR1, —COOR1, —NR1R1, —NR1$SO_2$R1, substituted aryl, substituted heteroaryl, substituted benzyl, substituted benzoyl, substituted phenoxy, unsubstituted aryl, and unsubstituted heteroaryl, unsubstituted benzyl, unsubstituted benzoyl, and unsubstituted phenoxy; and
$Y_2$, $Y_3$, $Y_4$, $Y_5$, and $Y_6$ are each independently selected from the group consisting of H, halogen, nitro, hydroxyl, cyano, $C_1$-$C_4$ alkyl, $C_1$-$C_4$ alkoxy, $C_2$-$C_4$ alkenyl, $C_2$-$C_4$ alkynyl, $C_1$-$C_4$ alkylthio, $C_1$-$C_4$ haloalkyl, $C_1$-$C_4$ haloalkoxy, $C_2$-$C_4$ haloalkenyl, $C_2$-$C_4$ haloalkynyl, $C_1$-$C_4$ haloalkylthio, —$SO_2$R1, —SONR1R1, —CR1=NOR1, —CONR1R1, —NR1COOR1, —COOR1, —NR1R1, —NR1$SO_2$R1, substituted aryl, substituted heteroaryl, substituted benzyl, substituted benzoyl, substituted phenoxy, unsubstituted aryl, unsubstituted heteroaryl, unsubstituted benzyl, unsubstituted benzoyl and unsubstituted phenoxy;
with the proviso that $X_3$ and $X_4$, $X_4$ and $X_5$, $X_5$ and $X_6$, $Y_2$ and $Y_3$, or $Y_3$ and $Y_4$ may form a 5- or 6-membered fused ring which may contain up to two heteroatoms selected from the group consisting of O, N, and S.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "cycloalkyl" refers to a monocyclic or polycyclic, saturated substituent consisting of carbon and hydrogen.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, or $C_3$-$C_6$ halocycloalkyl, unless stated otherwise.

The term "alkoxy" refers to an —OR substituent.

The term "alkylthio" refers to an —SR substituent.

The term "haloalkylthio" refers to an alkylthio, which is substituted with Cl, F, I, or Br or any combination thereof.

The term "cyano" refers to a —C≡N substituent.

The term "hydroxyl" refers to an —OH substituent.

The term "haloalkoxy" refers to an alkoxy substituent, which is substituted with Cl, F, Br, or I, or any combination thereof.

The term "haloalkyl" refers to an alkyl, which is substituted with Cl, F, I, or Br or any combination thereof.

The term "halocycloalkyl" refers to a monocyclic or polycyclic, saturated substituent consisting of carbon and hydrogen, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "aryl" refers to a cyclic, aromatic substituent consisting of hydrogen and carbon.

The term "heteroaryl" refers to a cyclic substituent that may be fully unsaturated, where the cyclic structure contains at least one carbon and at least one heteroatom, where said heteroatom is nitrogen, sulfur, or oxygen.

The term "phenoxy" refers to an —O substituted with a six-membered fully unsaturated ring consisting of hydrogen and carbon.

The term "benzyl" refers to a —$CH_3$ substituted with a six-membered fully unsaturated ring consisting of hydrogen and carbon.

The term "benzoyl" refers to a carbonyl substituted with a six-membered fully unsaturated ring consisting of hydrogen and carbon The term "nitro" refers to a —$NO_2$ substituent.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric or tautomeric forms of the molecule.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The embodiments of the invention described herein are not intended to be exhaustive or to limit the invention to the precise forms disclosed. Rather, the embodiments selected for description have been chosen to enable one skilled in the art to practice the invention. Although the disclosure is described as a synergistic combination of copper, copper based algicides, or other copper-containing materials and a hydrazone or hydrazone derivative it should be understood that the concepts presented herein may be used in various applications and should not be limited.

The mixtures of the present invention may have broad spectrum algicidal activity. Algae which may be controlled by the method of the present invention include individual species and mixed cultures. Examples of species controlled include green algae such as *Chlamydomonas reinhardtii, Chlorella pyrenoidosa, Scenedesmus quadricauda, Chlorococcum oleofaciens,* and *Selenastrum* species; blue-green algae (cyanobacteria) such as *Phormidium* species, *Anabaena flosaquae, Nostoc commune, Osiffiatorae* species, *Synechocystis* species, and *Synechococcus* species; and marine algae such as *Dunaliella parva.*

According to the method of the present invention, the mixtures described herein may be combined with other known antialgal compounds including: chlorine/bromine compounds; glutaraldehyde, isothiazoles, isothiazolones, organotin formulations, quaternary ammonium compounds, and triazines.

The amount of the active mixture required to control algae will depend upon many factors such as, for example: the type of surface; the amount of water present; whether the active mixture is incorporated into a coating composition, applied directly to an object, or added to an aqueous or other solution; and the type and extent of algal infestation.

While the mixtures described herein may be administered alone to control algae, it is preferable to administer them as formulations. Useful formulations comprise one or more compounds and one or more acceptable carriers. The term "acceptable carrier" means a carrier compatible with the active mixture and other ingredients of the formulation and which is not toxic to the system or which will not cause degradation of the system. Formulations of the mixtures may contain from 0.01 to 99.9 percent by weight of the mixture. More typically the solutions and formulations will contain from 1.0 to 85 percent by weight of the mixture. Useful formulations include aqueous solutions, solvent based solutions, wettable powders, emulsifiable concentrates, dusts, granular formulations, pellets, aerosols, or flowable emulsion concentrates. In such formulations, the compounds are extended with liquid or solid carriers and, when desired, suitable surfactants are incorporated.

In the case of spray formulations, it is often desirable to include one or more adjuvants, such as wetting agents, spreading agents, dispersing agents, stickers, adhesives, emulsifying agents and the like. Such adjuvants commonly used in the art can be found in the John W. McCutcheon, Inc. publication *Detergents and Emulsifiers, Annual*, Allured Publishing Company, Ridgewood, N.J., U.S.A. Spray formulations can be administered using common application methods, such as conventional high-volume hydraulic sprays, low-volume sprays, air-blast spray, aerial sprays, backpack and hand held sprays, and dusts. The dilution and rate of application will depend upon the type of equipment employed, the method of application, area treated, and algae to be controlled.

The mixtures of the present invention may also be used to control algae in cooling tower waters. In such applications the hydrazone and copper components of the mixtures are maintained at a concentration of from 0.001 ppm to the solubility limit of the compound, preferably 0.01 to 200 ppm.

In addition, the compounds of the present invention are useful for imparting algal resistance to coatings or impregnated compositions. In such applications, the mixtures are incorporated into the coating or into the impregnating composition at a concentration from 0.1 to 10 percent by weight, preferably 1 to 5 percent by weight.

The compounds of the present invention may also be useful for imparting algal resistance to construction products such as stucco, roof mastics, wall mastics, and masonry coatings; in clear finishes and coatings to protect underlying substrates from algae; for algae control in aquaculture including aquaria, fish hatcheries, shrimp ponds, finfish ponds, mollusk and crustacean cultivation; for algae control in recreational and decorative bodies of water such as swimming pools, lakes, fountains, and decorative ponds; for algae control in bodies of water for industrial or municipal use, such as settling or separation ponds, waste treatment ponds, and water reservoirs; for algae control in hydroponic farming or rice paddies; for algae control in processing and manufacture of pulp and paper products; and for inclusion in plastics or in coatings for plastics to protect against algae. Care must be taken in the selection of compound and application rate to avoid adverse effects on non-target organisms.

The mixtures have broad ranges of efficacy as algicides. The exact amounts of hydrazones and copper-containing materials to be applied is dependent not only on the specific materials being applied and relative amounts of hydrazone and copper in the mixtures, but also on the particular action desired, the algal species to be controlled, and the stage of growth thereof, as well as the location to be contacted with the mixture. Thus, all the mixtures, and formulations containing the same, may not be equally effective at similar concentrations or against the same algal species.

The exact amount of a mixture required varies with the algal species to be controlled, the type of formulation employed, the method of application, climate conditions, and the like. The dilution and rate of application will depend upon the type of equipment employed, the method and frequency of application desired and algal species to be controlled. The molar ratio of copper to hydrazone in the active mixture may range from 0.1:1 to 10,000:1, preferably from 0.5:1 to 1000:1 and more preferably from 1:1 to 20:1.

It should be understood that the preferred amount of a copper material to be mixed with hydrazone in a given application may be influenced by availability of copper from other sources such as copper present in the body of water or material to be treated, copper present in the water or solvent used in preparing the algicidal solutions for application such as in spray application, copper present in formulations used in preparing spray solutions or dusts for application, or any other suitable copper source.

For algal control the hydrazone may be applied before or after the application of copper such that the mixture is generated in the location where control is desired. Additionally, multiple applications of copper or the hydrazone may be applied.

As exemplified below, hydrazones of the present invention, or their metal complexes, in a mixture with inorganic or organic mono- or divalent copper salts or chelates (hereinafter referred to as "copper products") increase the biological potency of copper products, enabling comparable or improved efficacy at lower copper use rates. While not intending to be all-inclusive, copper products which may be mixed with the compounds of the present invention to provide enhanced potency may include the following: copper oxychloride, copper octanoate, copper ammonium carbonate, copper arsenate, copper oxysulfate, copper formate, copper propionate, copper oxyacetate, copper citrate, copper chloride, copper diammonium chloride, copper nitrate, copper carbonate, copper phosphate, copper pyrophosphate, copper disodium EDTA, copper diammonium EDTA, copper oxalate, copper tartrate, copper gluconate, copper glycinate, copper glutamate, copper aspartate, copper adipate, copper palmitate, copper stearate, copper caprylate, copper decanoate, copper undecylenate, copper neodecanoate, copper linoleate, copper oleate, copper borate, copper methanesulfonate, copper sulfamate, copper acetate, copper hydroxide, copper oxide, copper oxychloride-sulfate, copper sulfate, basic copper sulfate, copper-oxine, copper 3-phenylsalicylate, copper chloride hydroxide, copper dimethyldithiocarbamate, ammonium copper sulfate, copper magnesium sulfate, copper naphthenate, copper ethanolamine, chromated copper arsenate, ammoniacal copper arsenate, ammoniacal copper zinc arsenate, ammoniacal copper borate, Bordeaux mixture, copper zinc chromate, cufraneb, cupric hydrazinium sulfate, cuprobam, nano-copper materials, copper didecyldimethylammonium chloride, Algimycin P11-C, Aquatrine, A&V-70, Cutrine-plus, Stocktrine II and K-Tea algicide and where appropriate the hydrates of such compounds.

Methods for preparation of salicylaldehyde benzoylhydrazones and 2-hydroxyphenylketone benzoylhydrazones from salicylaldehydes or 2-hydroxyphenyl ketones and a benzoic acid hydrazide are well known in the literature. In addition the preparation of metal complexes of these materials is also well known (see for example Ainscough et al. *J. Inorg. Biochem.* 1999, 77, 125-133, which is expressly incorporated by reference herein). Methods of preparation of precursor hydrazides are also well known. Hydrazides can be prepared, for example, from carboxylic acids such as in Maxwell et al., *J. Med. Chem.* 1984, 27, 1565-1570, and from carboxylic esters such as in Dydio et al., *J. Org. Chem.* 2009, 74, 1525-1530, which are expressly incorporated by reference herein. Thus, the synthesis of any benzoylhydrazone of the present invention and its metal complex(es) is fully described where the starting aldehyde or ketone, and the starting benzoic acid hydrazide, benzoic acid, or benzoic acid ester are described. The hydrazones disclosed may also be in the form of algicidally acceptable salts and hydrates. Examples 8 and 9 below provide typical methods for the preparation of such benzoylhydrazones. Example 12 below provides a general method for the preparation of their metal complexes The compounds of Formula I may, therefore, be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

EXAMPLE 1

Preparation of 2-hydroxy-3,5-bis-trifluoromethylbenzaldehyde

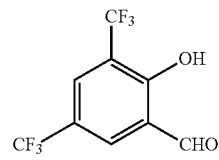 [SMILES: O=Cc1cc(C(F)(F)F)cc(C(F)(F)F)c1O]

3,5-Bis(trifluoromethyl)anisaldehyde (prepared as in Sui and Macielag, Synth. Commun. 1997, 27, 3581-3590, which is expressly incorporated by reference herein; 2.0 grams (g), 7.7 millimoles (mmol)) was dissolved in dry dichloromethane ($CH_2Cl_2$; 15 milliliters (mL)), cooled to −78° C. and treated in portions with boron tribromide ($BBr_3$, 1 M solution in $CH_2Cl_2$; 8.0 mL, 8.0 mmol). The mixture was stirred and allowed to warm to 25° C. After 20 hours (h), the mixture was cooled to −40° C., carefully treated with $H_2O$ (10 mL) and warmed to room temperature. The separated organic phase was washed with water ($H_2O$; 10 mL), saturated (satd) sodium chloride (NaCl) solution (5 mL), dried over sodium sulfate ($Na_2SO_4$) and evaporated. The residue was purified by silica gel chromatography with a 0 to 20% gradient of ethyl acetate (EtOAc) in hexane to give the purified aldehyde (1.4 g, 70%) as an oil: $^1$H NMR (400 MHz, $CDCl_3$) δ 12.05 (s, 1H), 10.02 (s, 1H), 8.07 (s, 2H). EIMS m/z 258.

EXAMPLE 2

Preparation of 5-chloro-2-hydroxy-3-trifluoromethylbenzaldehyde

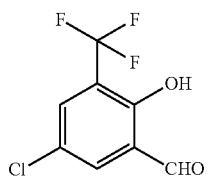 [SMILES: O=Cc1cc(Cl)cc(C(F)(F)F)c1O]

5-Chloro-2-fluorobenzotrifluoride (1.5 g, 7.5 mmol) was dissolved in dry tetrahydrofuran (THF; 10 mL), treated with tetramethylethylenediamine (TMEDA; 1.6 mL, 1.2 g, 11 mmol), cooled to −78° C. and treated in portions with n-butyl lithium (n-BuLi, 2.5 M in hexanes; 3.9 mL, 9.8 mmol). After stirring at −78° C. for 90 minutes (min), the mixture was treated with N,N-dimethylformamide (DMF; 770 microliters (μL), 730 mg, 10 mmol) and stirred for a further 30 min. The cooling bath was removed and mixture warmed to 25° C. over 30 min. The reaction was quenched by addition of satd ammonium chloride ($NH_4Cl$) solution then diluted with diethyl ether ($Et_2O$; 30 mL). The separated organic phase was washed with satd NaCl (10 mL), dried ($Na_2SO_4$) and evaporated. The residue was dissolved in dry methanol ($CH_3OH$; 10 mL) and treated with 30% sodium methoxide solution in $CH_3OH$ (14 g). The mixture was stirred at 25° C. for 20 h, diluted with $H_2O$ (50 mL) and extracted with $Et_2O$ (2×40 mL). The combined organic phases were washed with satd NaCl solution (20 mL), dried ($Na_2SO_4$) and evaporated. The residue was purified by silica gel chromatography using a 0 to 10% EtOAc gradient in hexane to give the benzaldehyde (1.1 g). This material (1.0 g, 4.2 mmol) was dissolved in dry $CH_2Cl_2$ (10 mL), cooled to −78° C. and treated with $BBr_3$ (1 M solution in $CH_2Cl_2$; 5 mL, 5 mmol). The mixture was allowed to warm to 25° C. and stirred for 22 h. After cooling to −45° C., the mixture was treated with $H_2O$ (5 mL), warmed to 25° C. and extracted with EtOAc (2×15 mL). The combined extracts were washed with satd NaCl solution (10 mL), dried ($Na_2SO_4$) and evaporated. The residue was purified by silica gel chromatography using a 0 to 10% EtOAc gradient in hexane to give the aldehyde (950 mg): $^1$H NMR (400 MHz, $CDCl_3$) δ 11.61 (s, 1H), 9.91 (s, 1H), 7.79 (d, J=2.5 Hz, 1H), 7.75 (d, J=2.6 Hz, 1H); EIMS m/z 224.

EXAMPLE 3

Preparation of 3-chloro-2-hydroxy-5-trifluoromethylbenzaldehyde

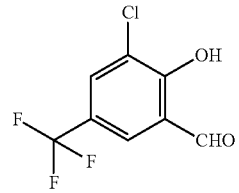

3-Chloro-2-fluoro-5-trifluoromethylbenzaldehyde (5.0 g, 22 mmol) was dissolved in dry $CH_3OH$ (50 mL), treated with 25% sodium methoxide solution (30 mL) and heated to reflux for 2 h. After cooling, the volatiles were removed by evaporation and the residue was taken up in $H_2O$ (20 mL) plus $Et_2O$ (80 mL). The aqueous phase was extracted with $Et_2O$ (50 mL), and the combined organic phases were washed with satd NaCl solution (15 mL), dried ($Na_2SO_4$) and evaporated. The residue was dissolved in dry $CH_2Cl_2$ (50 mL), cooled to −78° C. and treated with $BBr_3$ (1 M solution in $CH_2Cl_2$; 25 mL, 25 mmol). After warming to 25° C., the mixture was stirred for 21 h, cooled to −40° C. and quenched by addition of $H_2O$ (30 mL). After warming, the aqueous phase was extracted with $CH_2Cl_2$ (30 mL), and the combined organic phases were washed with satd NaCl solution (30 mL), dried ($Na_2SO_4$) and evaporated. The residue was purified by silica gel chromatography with a 0-20% EtOAc gradient in hexane to give the purified aldehyde (2.7 g): $^1$H NMR (400 MHz, $CDCl_3$) δ 11.81 (s, 1H), 9.96 (s, 1H), 7.87 (d, J=2.1 Hz, 1H), 7.84-7.77 (m, 1H); EIMS m/z 224.

EXAMPLE 4

Preparation of 3-chloro-2-hydroxy-6-trifluoromethylbenzaldehyde

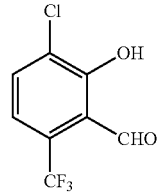

3-Chloro-2-fluoro-6-trifluoromethylbenzaldehyde (1.0 g, 4.4 mmol) was dissolved in dry $CH_3OH$ (10 mL), treated with 30% sodium methoxide solution in $CH_3OH$ (7.9 g, 44 mmol) and heated at reflux for 1 h. After cooling, the mixture was diluted with $H_2O$ (15 mL) and extracted with $Et_2O$ (30 mL). The combined organic extracts were washed with satd NaCl solution (10 mL), dried ($Na_2SO_4$), and evaporated. The residue was purified by silica gel chromatography with a 0-10% EtOAc gradient in hexane to give the anisole intermediate (1.0 g). This material was dissolved in dry $CH_2Cl_2$ (15 mL), cooled to −78° C., treated with $BBr_3$ (1 M in $CH_2Cl_2$; 5.0 mL, 5 mmol), allowed to warm to 25° C. and stirred for 20 h. The reaction was cooled in ice and quenched by addition of H₂O (10 mL). The separated organic phase was washed with satd NaCl solution (10 mL), dried (Na₂SO₄) and evaporated. The residue was purified by silica gel chromatography with a 0-10% EtOAc gradient in hexane to give the aldehyde (980 mg): ¹H NMR (400 MHz, CDCl₃) δ 12.78 (s, 1H), 10.28 (s, 1H), 7.71 (d, J=8.2 Hz, 1H), 7.27 (d, J=8.5 Hz, 1H); EIMS m/z 224.

EXAMPLE 5

Preparation of 3,4-dichloro-2-hydroxybenzaldehyde

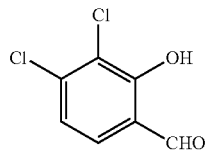 [SMILES: O=Cc1ccc(Cl)c(Cl)c1O]

3,4-Dichloro-2-hydroxybenzaldehyde was prepared from commercially available starting materials as described in Gu et al., *J. Med. Chem.* 2000, 43, 4868-4876, which is expressly incorporated by reference herein.

EXAMPLE 6

Preparation of 3,6-dichloro-2-hydroxybenzaldehyde

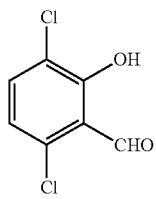 [SMILES: O=Cc1c(Cl)ccc(Cl)c1O]

3,6-Dichloro-2-hydroxybenzaldehyde was prepared from commercially available starting materials as described in Rafferty et al., PCT Int. Appl. WO 2008121602 A1, which is expressly incorporated by reference herein.

EXAMPLE 7

Preparation of 2-hydroxy-5-trifluoromethylbenzaldehyde

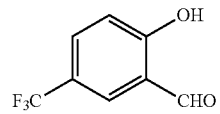

2-Hydroxy-5-trifluoromethylbenzaldehyde was prepared from commercially available starting materials as described in Bonnert et al., PCT Int. Appl. WO 2006056752 A1, which is expressly incorporated by reference herein.

EXAMPLE 8

Preparation of 4-chlorobenzoic acid [1-(2-chloro-6-hydroxyphenyl)-methylidene]-hydrazide (Compound 70)

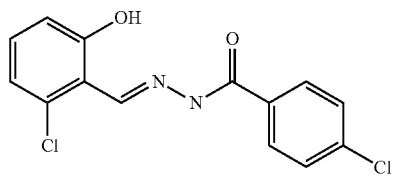 [SMILES: O=C(N/N=C/c1c(O)cccc1Cl)c1ccc(Cl)cc1]

A suspension of 2-chloro-6-hydroxybenzaldehyde (0.10 g, 0.64 mmol) and 4-chlorobenzoic acid hydrazide (0.10 g, 0.61 mmol) in EtOH (3 mL) was agitated and heated to 60° C. for 16 h. The reaction mixture was cooled to room temperature and H₂O (1-2 mL) was added portionwise to precipitate the product. The solid was collected via suction filtration and rinsed with ethanol to furnish the title compound as an off-white solid (0.18 g, 95%): mp 273-277° C.; ¹H NMR (400 MHz, DMSO-d₆) δ 12.53 (s, 1H), 12.51 (s, 1H), 9.04 (s, 1H), 8.03-7.95 (m, 2H), 7.71-7.63 (m, 2H), 7.34 (t, J=8.2 Hz, 1H), 7.07 (dd, J=7.9, 0.9 Hz, 1H), 6.96 (d, J=8.2 Hz, 1H); ESIMS m/z 309 ([M+H]⁺), 307 ([M−H]⁻).

EXAMPLE 9

Preparation of 3-methyl-benzoic acid [1-(3,5-dichloro-2-hydroxyphenyl)-ethylidene]-hydrazide (Compound 25)

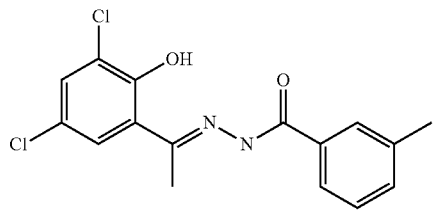 [SMILES: C/C(=N\NC(=O)c1cccc(C)c1)c1cc(Cl)cc(Cl)c1O]

A suspension of 1-(3,5-dichloro-2-hydroxyphenyl)-ethanone (0.100 g, 0.49 mmol), 3-methylbenzoic acid hydrazide (0.069 g, 0.46 mmol), and glacial acetic acid (0.3 mL) in EtOH (3 mL) was heated to 60° C. for 4 h The reaction mixture was cooled to room temperature to precipitate the product. The solid was collected via suction filtration and rinsed with H₂O to furnish the title material as a yellow solid (0.144 g, 93%): mp 221-223° C.; ¹H NMR (400 MHz, DMSO) δ 14.48 (s, 1H), 11.54 (s, 1H), 7.79-7.72 (m, 2H), 7.68 (d, J=2.5 Hz, 1H), 7.64 (d, J=2.4 Hz, 1H), 7.47-7.42 (m, 2H), 2.52 (s, 3H), 2.41 (s, 3H); ESIMS m/z 337 ([M+H]⁺), 335 ([M−H]⁻).

TABLE 1

Structures of Exemplified Compounds

| Compound Number | Structure |
|---|---|
| 1 | 3,5-dichloro-2-hydroxybenzaldehyde benzoyl hydrazone |
| 2 | 1-(2-hydroxyphenyl)ethanone benzoyl hydrazone |
| 3 | 5-chloro-2-hydroxybenzaldehyde benzoyl hydrazone |
| 4 | 3,5-dichloro-2-hydroxybenzaldehyde 4-fluorobenzoyl hydrazone |
| 5 | 1-(3,5-dichloro-2-hydroxyphenyl)ethanone 2-bromobenzoyl hydrazone |
| 6 | 1-(3,5-dichloro-2-hydroxyphenyl)ethanone benzoyl hydrazone |
| 7 | 3,5-dichloro-2-hydroxybenzaldehyde 2-hydroxybenzoyl hydrazone |

TABLE 1-continued

Structures of Exemplified Compounds

| Compound Number | Structure |
|---|---|
| 8 | 3,5-dichloro-2-hydroxybenzaldehyde 3-chlorobenzoyl hydrazone |
| 9 | 3,5-dichloro-2-hydroxybenzaldehyde 4-bromobenzoyl hydrazone |
| 10 | 3,5-dichloro-2-hydroxybenzaldehyde 2-naphthoyl hydrazone |
| 11 | 3,5-dibromo-2-hydroxybenzaldehyde benzoyl hydrazone |
| 12 | 1-(3,5-dichloro-2-hydroxyphenyl)ethanone 4-chlorobenzoyl hydrazone |
| 13 | 1-(3,5-dichloro-2-hydroxyphenyl)ethanone phenylacetyl hydrazone |
| 14 | 3-bromo-5-chloro-2-hydroxybenzaldehyde benzoyl hydrazone |

TABLE 1-continued

Structures of Exemplified Compounds

| Compound Number | Structure |
|---|---|
| 15 | 3-bromo-5-chloro-2-hydroxybenzaldehyde N'-(4-chlorobenzoyl)hydrazone |
| 16 | 3-bromo-5-chloro-2-hydroxybenzaldehyde N'-(2-methylbenzoyl)hydrazone |
| 17 | 3-bromo-5-chloro-2-hydroxybenzaldehyde N'-(3-bromobenzoyl)hydrazone |
| 18 | 3-bromo-5-chloro-2-hydroxybenzaldehyde N'-(2-hydroxybenzoyl)hydrazone |
| 19 | 5-bromo-2-hydroxy-3-methoxybenzaldehyde N'-(3-bromobenzoyl)hydrazone |
| 20 | 5-bromo-2-hydroxy-3-methoxybenzaldehyde N'-(4-methylbenzoyl)hydrazone |
| 21 | 3,4-dichloro-2-hydroxybenzaldehyde N'-benzoylhydrazone |
| 22 | 3,5-dichloro-2-hydroxybenzaldehyde N'-(3-trifluoromethylbenzoyl)hydrazone |
| 23 | 2-hydroxy-3-nitroacetophenone N'-(4-chlorobenzoyl)hydrazone |
| 24 | 3-chloro-2-hydroxy-5-trifluoromethylbenzaldehyde N'-benzoylhydrazone |
| 25 | 3,5-dichloro-2-hydroxyacetophenone N'-(3-methylbenzoyl)hydrazone |
| 26 | 3,5-dichloro-2-hydroxyacetophenone N'-(4-methylbenzoyl)hydrazone |

TABLE 1-continued

Structures of Exemplified Compounds

| Compound Number | Structure |
|---|---|
| 27 | 5-chloro-3-(trifluoromethyl)-2-hydroxybenzaldehyde benzoyl hydrazone |
| 28 | 3-chloro-5-(trifluoromethyl)-2-hydroxybenzaldehyde 3-fluorobenzoyl hydrazone |
| 29 | 3-chloro-5-(trifluoromethyl)-2-hydroxybenzaldehyde 4-fluorobenzoyl hydrazone |
| 30 | 3-chloro-5-(trifluoromethyl)-2-hydroxybenzaldehyde 2-hydroxybenzoyl hydrazone |
| 31 | 3-chloro-5-(trifluoromethyl)-2-hydroxybenzaldehyde 2-hydroxy-4-methylbenzoyl hydrazone |
| 32 | 3,5-bis(trifluoromethyl)-2-hydroxybenzaldehyde 4-chlorobenzoyl hydrazone |
| 33 | 3-(trifluoromethyl)-2-hydroxybenzaldehyde 3-methylbenzoyl hydrazone |
| 34 | 3-(trifluoromethyl)-2-hydroxybenzaldehyde 3-fluorobenzoyl hydrazone |
| 35 | 3-(trifluoromethyl)-2-hydroxybenzaldehyde 4-chlorobenzoyl hydrazone |
| 36 | 3-(trifluoromethyl)-2-hydroxybenzaldehyde 2-hydroxybenzoyl hydrazone |
| 37 | 3-(trifluoromethyl)-2-hydroxybenzaldehyde 2-hydroxy-4-methylbenzoyl hydrazone |
| 38 | 3,4-dichloro-2-hydroxybenzaldehyde 3-methylbenzoyl hydrazone |

TABLE 1-continued

Structures of Exemplified Compounds

| Compound Number | Structure |
|---|---|
| 39 | 3,4-dichloro-2-hydroxybenzaldehyde 3-fluorobenzoylhydrazone |
| 40 | 3,4-dichloro-2-hydroxybenzaldehyde 3-chlorobenzoylhydrazone |
| 41 | 3,4-dichloro-2-hydroxybenzaldehyde 2-hydroxy-4-methylbenzoylhydrazone |
| 42 | 3,6-dichloro-2-hydroxybenzaldehyde 3-methylbenzoylhydrazone |
| 43 | 3,6-dichloro-2-hydroxybenzaldehyde 4-fluorobenzoylhydrazone |
| 44 | 3,6-dichloro-2-hydroxybenzaldehyde 3-chlorobenzoylhydrazone |
| 45 | 3,6-dichloro-2-hydroxybenzaldehyde 4-chlorobenzoylhydrazone |
| 46 | 3,6-dichloro-2-hydroxybenzaldehyde 2-hydroxybenzoylhydrazone |
| 47 | 5-chloro-2-hydroxy-3-(trifluoromethyl)benzaldehyde 3-chlorobenzoylhydrazone |
| 48 | 5-chloro-2-hydroxy-3-(trifluoromethyl)benzaldehyde 2-hydroxybenzoylhydrazone |
| 49 | 3-chloro-2-hydroxybenzaldehyde 4-nitrobenzoylhydrazone |
| 50 | 3-chloro-2-hydroxybenzaldehyde 3-methylbenzoylhydrazone |

TABLE 1-continued

Structures of Exemplified Compounds

| Compound Number | Structure |
|---|---|
| 51 | 3-chloro-2-hydroxybenzaldehyde 3-chlorobenzoyl hydrazone |
| 52 | 3-chloro-2-hydroxybenzaldehyde 4-chlorobenzoyl hydrazone |
| 53 | 3-chloro-2-hydroxybenzaldehyde 4-nitrobenzoyl hydrazone |
| 54 | 3-chloro-2-hydroxybenzaldehyde 2-hydroxybenzoyl hydrazone |
| 55 | 3-chloro-2-hydroxybenzaldehyde 2-hydroxy-4-methylbenzoyl hydrazone |
| 56 | 3-chloro-2-hydroxy-6-(trifluoromethyl)benzaldehyde 4-chlorobenzoyl hydrazone |
| 57 | 3-chloro-2-hydroxy-6-(trifluoromethyl)benzaldehyde 2-hydroxybenzoyl hydrazone |
| 58 | 1-(3,5-dichloro-2-hydroxyphenyl)ethanone 2-hydroxy-6-methylbenzoyl hydrazone |
| 59 | 1-(3-chloro-2-hydroxyphenyl)ethanone 4-methylbenzoyl hydrazone |
| 60 | 1-(2-hydroxy-3-nitrophenyl)ethanone 4-bromobenzoyl hydrazone |
| 61 | 1-(3,5-dibromo-2-hydroxyphenyl)ethanone benzoyl hydrazone |
| 62 | 1-(3,5-difluoro-2-hydroxyphenyl)ethanone 4-chlorobenzoyl hydrazone |

TABLE 1-continued
Structures of Exemplified Compounds
| Compound Number | Structure |
|---|---|
| 63 | 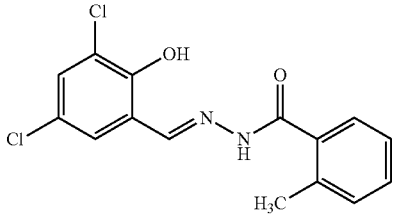 |
| 64 | 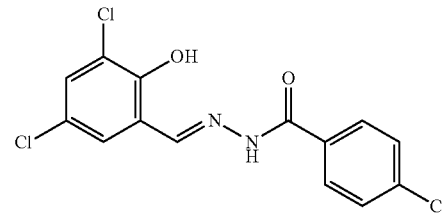 [SMILES: O=C(N/N=C/c1cc(Cl)cc(Cl)c1O)c1ccc(F)cc1] |
| 65 | 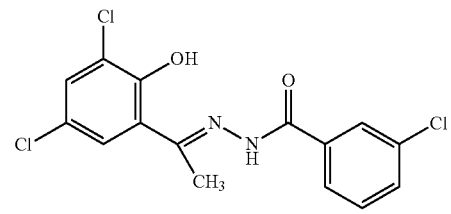 [SMILES: C/C(=N\NC(=O)c1cccc(Cl)c1)c1cc(Cl)cc(Cl)c1O] |
| 66 | 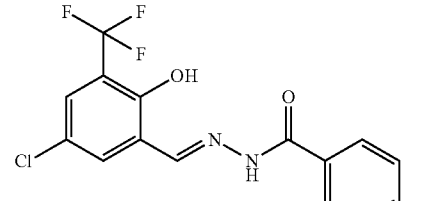 |
| 67 | 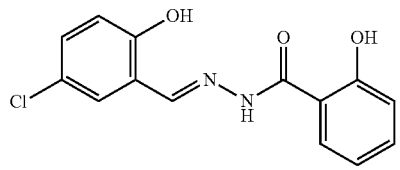 [SMILES: O=C(N/N=C/c1cc(Cl)ccc1O)c1ccccc1O] |
| 68 | 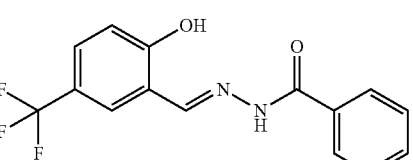 |
| 69 | 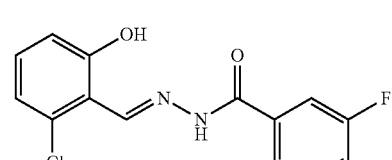 |
| 70 | 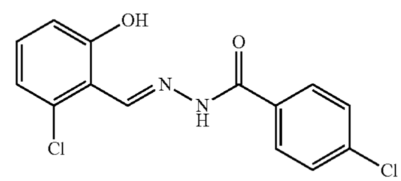 [SMILES: O=C(N/N=C/c1c(O)cccc1Cl)c1ccc(Cl)cc1] |
| 71 | 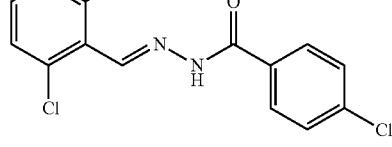 |
TABLE 2
Analytical Data for Compounds in Table 1
| Compound Number | mp (° C.) | ESIMS (+) | ESIMS (−) | $^1$H NMR (400 MHz, DMSO-$d_6$) δ, unless otherwise stated |
|---|---|---|---|---|
| 1 | | 309 | 307 | |
| 2 | 185-187 | 255 | 253 | (300 MHz, CDCl$_3$) 12.73 (s, 1H), 9.00 (s, 1H), 7.90-7.82 (m, 2H), 7.64-7.57 (m, 1H), 7.55-7.47 (m, 3H), 7.35-7.28 (m, 1H), 7.09-7.00 (m, 1H), 6.94-6.87 (m, 1H), 2.42 (s, 3H) |
| 3 | | 275 | 273 | |
| 4 | | 327 | 325 | |
| 5 | 220-222 | 403 | 401 | 14.32 (s, 1H), 11.91 (s, 1H), 7.76 (dd, J = 7.8, 1.1 Hz, 1H), 7.67 (d, J = 2.5 Hz, 1H), 7.65 (d, J = 2.4 Hz, 1H), 7.61 (dd, J = 7.4, 1.8 Hz, 1H), 7.55-7.45 (m, 2H), 2.45 (s, 3H) |
| 6 | | 345 (M + Na) | 321 | |
| 7 | | | 323 | |
| 8 | | 343 | 341 | |
| 9 | | | 385 | |

TABLE 2-continued

Analytical Data for Compounds in Table 1

| Compound Number | mp (° C.) | ESIMS (+) | ESIMS (−) | ¹H NMR (400 MHz, DMSO-d$_6$) δ, unless otherwise stated |
|---|---|---|---|---|
| 10 | 215-217 | 359 | | 12.70 (s, 1H), 12.60 (s, 1H), 8.63 (s, 1H), 8.60 (s, 1H), 8.13-8.07 (m, 2H), 8.06-8.00 (m, 2H), 7.73-7.62 (m, 4H) |
| 11 | | 421 (M + Na) | 397 | |
| 12 | 260-262 | | 355 | 14.41 (s, 1H), 11.65 (s, 1H), 7.99 (d, J = 8.5 Hz, 2H), 7.68 (d, J = 2.5 Hz, 1H), 7.66-7.60 (m, 3H), 2.68-2.32 (m, 3H) |
| 13 | 199-204 | 338 | 336 | 14.27 (s, 1H), 11.44 (s, 1H), 7.61 (dd, J = 10.6, 2.5 Hz, 2H), 7.36-7.32 (m, 4H), 7.30-7.23 (m, 1H), 3.75 (s, 2H), 2.44 (s, 3H) |
| 14 | | 374 (M + Na) | 351 | |
| 15 | | 411 (M + Na) | | |
| 16 | | 367 | | |
| 17 | | 456 (M + Na) | | |
| 18 | | | 367 | |
| 19 | | 429 | 427 | |
| 20 | | 363 | 361 | |
| 21 | 249-252 | 289 | 287 | 12.88 (s, 1H), 12.46 (s, 1H), 8.61 (s, 1H), 8.04-7.89 (m, 2H), 7.60 (ddd, J = 12.6, 11.5, 6.4 Hz, 4H), 7.23 (d, J = 8.4 Hz, 1H) |
| 22 | 165-169 | | 375 | 12.70 (s, 1H), 12.38 (s, 1H), 8.60 (s, 1H), 8.32-8.23 (m, 2H), 8.02 (d, J = 7.8 Hz, 1H), 7.83 (t, J = 7.8 Hz, 1H), 7.68 (dd, J = 24.6, 2.5 Hz, 2H) |
| 23 | 241-251 | 334 | 332 | 15.17 (s, 1H), 11.70 (s, 1H), 7.99 (d, J = 8.5 Hz, 3H), 7.94 (dd, J = 8.1, 1.4 Hz, 1H), 7.65 (d, J = 8.5 Hz, 2H), 7.06 (t, J = 8.0 Hz, 1H), 2.56 (s, 3H) |
| 24 | 216-222 | 343 | 341 | 13.24 (s, 1H), 12.64 (s, 1H), 8.69 (s, 1H), 8.04-7.88 (m, 4H), 7.62 (dt, J = 31.2, 7.3 Hz, 3H) |
| 25 | 221-223 | 337 | 335 | 14.48 (s, 1H), 11.54 (s, 1H), 7.79-7.72 (m, 2H), 7.68 (d, J = 2.5 Hz, 1H), 7.64 (d, J = 2.4 Hz, 1H), 7.47-7.42 (m, 2H), 2.52 (s, 3H), 2.41 (s, 3H) |
| 26 | 262-264 | 337 | 335 | |
| 27 | 225-226 | 343 | 341 | 13.15 (s, 1H), 12.64 (s, 1H), 8.61 (s, 1H), 8.04-7.90 (m, 3H), 7.75-7.52 (m, 4H) |
| 28 | 210-212 | 361 | 359 | 13.15 (s, 1H), 12.69 (s, 1H), 8.69 (s, 1H), 8.03 (s, 1H), 7.91 (d, J = 1.8 Hz, 1H), 7.80 (dd, J = 19.3, 8.7 Hz, 2H), 7.64 (d, J = 5.8 Hz, 1H), 7.52 (d, J = 1.9 Hz, 1H) |
| 29 | 200-202 | 361 | 359 | 13.4 (s, 1H), 12.66 (s, 1H), 8.68 (s, 1H), 8.11-7.98 (m, 2H), 7.90 (d, J = 2.1 Hz, 1H), 7.43 (t, J = 8.8 Hz, 2H), 7.35-7.24 (m, 1H) |
| 30 | 258-260 | 359 | 357 | 13.11 (s, 1H), 12.35 (s, 1H), 11.45 (s, 1H), 8.73 (s, 1H), 7.98 (d, J = 1.7 Hz, 1H), 7.95-7.83 (m, 2H), 7.54-7.40 (m, 1H), 7.00 (dd, J = 14.0, 7.4 Hz, 2H) |
| 31 | 255-257 | 373 | 371 | 13.09 (s, 1H), 12.37 (s, 1H), 11.63 (s, 1H), 8.72 (s, 1H), 7.97 (d, J = 1.7 Hz, 1H), 7.90 (d, J = 1.8 Hz, 1H), 7.81 (d, J = 8.5 Hz, 1H), 6.81 (d, J = 8.5 Hz, 2H), 2.32 (d, J = 6.7 Hz, 3H) |
| 32 | 233-236 | 411 | 409 | 13.85 (s, 1H), 12.84 (s, 1H), 8.71 (s, 1H), 8.36 (s, 1H), 8.00 (d, J = 8.5 Hz, 2H), 7.94 (s, 1H), 7.67 (d, J = 8.5 Hz, 2H) |

TABLE 2-continued

Analytical Data for Compounds in Table 1

| Compound Number | mp (° C.) | ESIMS (+) | ESIMS (−) | $^1$H NMR (400 MHz, DMSO-$d_6$) δ, unless otherwise stated |
|---|---|---|---|---|
| 33 | 188-190 | 323 | 321 | 13.03 (s, 1H), 12.44 (s, 1H), 8.64 (s, 1H), 7.82-7.72 (m, 3H), 7.67 (d, J = 7.3 Hz, 1H), 7.46 (d, J = 5.0 Hz, 2H), 7.11 (t, J = 7.8 Hz, 1H), 2.41 (s, 3H) |
| 34 | 176-180 | 327 | 325 | (300 MHz) 12.92 (s, 1H), 12.54 (s, 1H), 8.65 (s, 1H), 7.86-7.73 (m, 3H), 7.72-7.59 (m, 2H), 7.51 (td, J = 8.5, 2.2 Hz, 1H), 7.12 (t, J = 7.7 Hz, 1H) |
| 35 | 215-216 | 343 | 341 | 12.96 (s, 1H), 12.55 (s, 1H), 8.64 (s, 1H), 7.99 (d, J = 8.6 Hz, 2H), 7.81 (d, J = 7.5 Hz, 1H), 7.71-7.63 (m, 3H), 7.11 (t, J = 7.7 Hz, 1H) |
| 36 | 230-234 | 325 | 323 | 12.95 (s, 1H), 12.28 (s, 1H), 11.56 (s, 1H), 8.71 (s, 1H), 7.88 (dd, J = 7.9, 1.6 Hz, 1H), 7.79 (d, J = 7.6 Hz, 1H), 7.68 (d, J = 7.1 Hz, 1H), 7.52-7.44 (m, 1H), 7.12 (t, J = 7.8 Hz, 1H), 7.05-6.96 (m, 2H) |
| 37 | 248-253 | 339 | 337 | 12.95 (s, 1H), 12.26 (s, 1H), 11.67 (s, 1H), 8.70 (s, 1H), 7.80 (t, J = 9.1 Hz, 2H), 7.67 (d, J = 7.4 Hz, 1H), 7.11 (t, J = 7.8 Hz, 1H), 6.83 (d, J = 7.4 Hz, 2H), 2.31 (s, 3H) |
| 38 | 212-214 | 323 | 321 | 12.89 (s, 1H), 12.41 (s, 1H), 8.60 (s, 1H), 7.79-7.70 (m, 2H), 7.54 (d, J = 8.5 Hz, 1H), 7.45 (d, J = 4.4 Hz, 2H), 7.24 (d, J = 8.4 Hz, 1H), 2.41 (s, 3H) |
| 39 | 215-218 | 327 | 325 | 12.75 (s, 1H), 12.50 (s, 1H), 8.61 (s, 1H), 7.81 (d, J = 7.8 Hz, 1H), 7.79-7.73 (m, 1H), 7.67-7.59 (m, 1H), 7.58 (d, J = 8.5 Hz, 1H), 7.51 (td, J = 8.4, 2.4 Hz, 1H), 7.24 (d, J = 8.4 Hz, 1H) |
| 40 | 219-222 | 343 | 341 | 12.73 (s, 1H), 12.52 (s, 1H), 8.60 (s, 1H), 8.00 (t, J = 1.8 Hz, 1H), 7.92 (d, J = 7.8 Hz, 1H), 7.74-7.69 (m, 1H), 7.61 (t, J = 7.9 Hz, 1H), 7.57 (d, J = 8.5 Hz, 1H), 7.24 (d, J = 8.4 Hz, 1H) |
| 41 | 271-278 | 339 | 337 | 12.79 (s, 1H), 12.24 (s, 1H), 11.69 (s, 1H), 8.66 (s, 1H), 7.80 (d, J = 8.6 Hz, 1H), 7.54 (d, J = 8.5 Hz, 1H), 7.24 (d, J = 8.4 Hz, 1H), 6.84-6.79 (m, 2H), 2.31 (s, 3H) |
| 42 | 214-216 | 323 |  | 13.46 (s, 1H), 12.57 (s, 1H), 9.01 (s, 1H), 7.82-7.75 (m, 2H), 7.53 (d, J = 8.6 Hz, 1H), 7.49-7.45 (m, 2H), 7.10 (d, J = 8.6 Hz, 1H), 2.42 (s, 3H) |
| 43 | 264-267 | 327 | 325 | 13.41 (s, 1H), 12.62 (s, 1H), 9.00 (s, 1H), 8.10-8.01 (m, 2H), 7.53 (d, J = 8.6 Hz, 1H), 7.44 (t, J = 8.8 Hz, 2H), 7.10 (d, J = 8.6 Hz, 1H) |
| 44 | 232-234 | 343 | 341 | 13.34 (s, 1H), 12.67 (s, 1H), 9.00 (s, 1H), 8.04-8.00 (m, 1H), 7.94 (d, J = 7.8 Hz, 1H), 7.74 (d, J = 9.0 Hz, 1H), 7.63 (t, J = 7.9 Hz, 1H), 7.54 (d, J = 8.6 Hz, 1H), 7.10 (d, J = 8.6 Hz, 1H) |
| 45 | 271-273 | 343 |  | 13.38 (s, 1H), 12.66 (s, 1H), 9.00 (s, 1H), 8.00 (d, J = 8.5 Hz, 2H), 7.67 (d, J = 8.5 Hz, 2H), 7.53 (d, J = 8.6 Hz, 1H), 7.10 (d, J = 8.6 Hz, 1H) |
| 46 | 260-262 | 325 | 323 | 13.43 (s, 1H), 12.46 (s, 1H), 11.48 (s, 1H), 9.06 (s, 1H), 7.86 (dd, J = 7.9, 1.6 Hz, 1H), 7.54 (d, J = 8.6 Hz, 1H), 7.52-7.45 (m, 1H), 7.10 (d, J = 8.6 Hz, 1H), 7.05-6.96 (m, 2H) |

TABLE 2-continued

Analytical Data for Compounds in Table 1

| Compound Number | mp (° C.) | ESIMS (+) | ESIMS (−) | $^1$H NMR (400 MHz, DMSO-d$_6$) δ, unless otherwise stated |
|---|---|---|---|---|
| 47 | 228-229 | 377 | 375 | 13.08 (s, 1H), 12.74 (s, 1H), 8.60 (s, 1H), 8.05-7.97 (m, 2H), 7.93 (d, J = 7.8 Hz, 1H), 7.72 (t, J = 5.3 Hz, 2H), 7.62 (t, J = 7.9 Hz, 1H) |
| 48 | 258-260 | 359 | 357 | 13.10 (s, 1H), 12.43 (s, 1H), 11.51 (s, 1H), 8.66 (s, 1H), 7.97 (d, J = 2.5 Hz, 1H), 7.87 (dd, J = 7.9, 1.5 Hz, 1H), 7.71 (d, J = 2.5 Hz, 1H), 7.55-7.39 (m, 1H), 7.06-6.91 (m, 2H) |
| 49 | >300 | 320 | 318 | 12.73 (s, 1H), 12.44 (s, 1H), 9.06 (s, 1H), 8.46-8.38 (m, 2H), 8.25-8.16 (m, 2H), 7.36 (t, J = 8.2 Hz, 1H), 7.08 (dd, J = 8.0, 0.9 Hz, 1H), 6.97 (d, J = 8.1 Hz, 1H) |
| 50 | 166-169 | 289 | 287 | (400 MHz, CDCl$_3$) 8.59 (d, J = 12.0 Hz, 1H), 7.76 (d, J = 10.0 Hz, 2H), 7.47 (dd, J = 15.6, 6.2 Hz, 4H), 6.97 (t, J = 7.8 Hz, 1H), 2.39 (d, J = 12.0 Hz, 3H) |
| 51 | 174-178 | 309 | 307 | (400 MHz, CDCl$_3$) 8.61 (s, 1H), 8.00 (t, J = 1.7 Hz, 1H), 7.95-7.68 (m, 2H), 7.61 (t, J = 7.9 Hz, 1H), 7.55-7.47 (m, 2H), 6.98 (t, J = 7.8 Hz, 1H) |
| 52 | 257-260 | 309 | 307 | 12.20 (s, 1H), 11.50 (s, 1H), 8.64 (s, 1H), 7.96 (d, J = 8.5 Hz, 2H), 7.67-7.60 (m, 3H), 7.03-6.94 (m, 2H) |
| 53 | 284-287 | 320 | 318 | (400 MHz, CDCl$_3$) 8.64 (s, 1H), 8.41 (d, J = 8.5 Hz, 2H), 8.19 (d, J = 8.6 Hz, 2H), 7.56-7.47 (m, 2H), 6.98 (t, J = 7.8 Hz, 1H) |
| 54 | 266-268 | 291 | 289 | (400 MHz, CDCl$_3$) 8.66 (s, 1H), 7.87 (dd, J = 7.9, 1.6 Hz, 1H), 7.54-7.42 (m, 3H), 6.98 (ddd, J = 7.8, 5.6, 3.9 Hz, 3H) |
| 55 | 258-266 | 305 | 303 | (400 MHz, CDCl$_3$) 8.66 (s, 1H), 7.80 (d, J = 8.6 Hz, 1H), 7.49 (dd, J = 7.9, 2.1 Hz, 2H), 6.98 (t, J = 7.8 Hz, 1H), 6.81 (d, J = 7.3 Hz, 2H), 2.31 (s, 3H) |
| 56 | 236-238 | 377 | 375 | 13.76 (s, 1H), 12.73 (s, 1H), 8.92 (s, 1H), 8.00 (d, J = 8.6 Hz, 2H), 7.72 (d, J = 8.3 Hz, 1H), 7.67 (d, J = 8.6 Hz, 2H), 7.36 (d, J = 8.4 Hz, 1H) |
| 57 | 278-280 | 358 | 356 | 13.82 (s, 1H), 12.57 (s, 1H), 11.28 (s, 1H), 8.98 (d, J = 1.3 Hz, 1H), 7.84 (dd, J = 7.9, 1.5 Hz, 1H), 7.73 (d, J = 8.3 Hz, 1H), 7.53-7.45 (m, 1H), 7.36 (d, J = 8.4 Hz, 1H), 7.01 (dd, J = 13.2, 7.7 Hz, 2H) |
| 58 | 245 | 352 | 351 | 14.55, 11.80, 11.69, 11.46, 9.82, 9.72 (6s, 3H), 7.64-7.50 (m, 2H), 7.16 (t, J = 7.9 Hz, 1H), 6.77-6.71 (m, 2H), 2.40, 2.38 (2s, 3H), 2.22, 2.14 (2s, 3H) Note: rotational isomers |
| 59 | 195-200 | 303 | 301 | 14.38 (s, 1H), 11.40 (s, 1H), 7.87 (d, J = 8.0 Hz, 2H), 7.64 (dd, J = 8.1, 1.5 Hz, 1H), 7.49 (dd, J = 7.9, 1.3 Hz, 1H), 7.37 (d, J = 8.0 Hz, 2H), 6.92 (t, J = 8.0 Hz, 1H), 2.51 (s, 3H), 2.40 (s, 3H) |
| 60 | 244-252 | 379 | | 15.16 (s, 1H), 11.70 (s, 1H), 8.02-7.87 (m, 4H), 7.79 (d, J = 8.5 Hz, 2H), 7.06 (t, J = 8.0 Hz, 1H), 2.56 (s, 3H) |
| 61 | 242-245 | 414 | | |
| 62 | 276-280 | 325 | 323 | 13.48 (s, 1H), 11.59 (s, 1H), 7.98 (d, J = 8.5 Hz, 2H), 7.64 (d, J = 8.5 Hz, 2H), 7.43-7.36 (m, 2H), 2.50 (s, 3H) |
| 63 | | 323 | 321 | |

TABLE 2-continued

Analytical Data for Compounds in Table 1

| Compound Number | mp (° C.) | ESIMS (+) | ESIMS (−) | $^1$H NMR (400 MHz, DMSO-$d_6$) δ, unless otherwise stated |
|---|---|---|---|---|
| 64 | | 343 | 341 | |
| 65 | 245-246 | 357 | 355 | 14.38 (s, 1H), 11.68 (s, 1H), 8.02 (s, 1H), 7.91 (d, J = 7.7 Hz, 1H), 7.72 (d, J = 9.1 Hz, 1H), 7.70 (d, J = 2.5 Hz, 1H), 7.65 (d, J = 2.4 Hz, 1H), 7.60 (t, J = 7.9 Hz, 1H), 2.53 (s, 3H) |
| 66 | 232-234 | 377 | 375 | 13.13 (s, 1H), 12.72 (s, 1H), 8.60 (s, 1H), 8.00 (dd, J = 10.9, 5.5 Hz, 3H), 7.71 (d, J = 2.4 Hz, 1H), 7.66 (d, J = 8.6 Hz, 2H) |
| 67 | | | | |
| 68 | 214-217 | 309 | 307 | 12.25 (s, 1H), 11.84 (s, 1H), 8.73 (s, 1H), 8.01 (s, 1H), 7.95 (d, J = 7.9 Hz, 2H), 7.59 (dt, J = 30.0, 7.5 Hz, 4H), 7.12 (d, J = 8.6 Hz, 1H) |
| 69 | 257-259 | 293 | 291 | 12.52 (s, 1H), 12.48 (s, 1H), 9.04 (s, 1H), 7.83 (d, J = 7.8 Hz, 1H), 7.80-7.75 (m, 1H), 7.68-7.60 (m, 1H), 7.52 (td, J = 8.5, 2.4 Hz, 1H), 7.35 (t, J = 8.2 Hz, 1H), 7.07 (d, J = 7.9 Hz, 1H), 6.97 (d, J = 8.3 Hz, 1H) |
| 70 | 273-277 | 309 | 307 | 12.53 (s, 1H), 12.51 (s, 1H), 9.04 (s, 1H), 8.03-7.95 (m, 2H), 7.71-7.63 (m, 2H), 7.34 (t, J = 8.2 Hz, 1H), 7.07 (dd, J = 7.9, 0.9 Hz, 1H), 6.96 (d, J = 8.2 Hz, 1H) |
| 71 | 277-281 | 325 | 323 | 12.15 (s, 1H), 11.78 (s, 2H), 8.75 (s, 1H), 8.01 (d, J = 1.8 Hz, 1H), 7.89 (dd, J = 7.8, 1.2 Hz, 1H), 7.65 (dd, J = 8.6, 2.1 Hz, 1H), 7.50-7.42 (m, 1H), 7.13 (d, J = 8.6 Hz, 1H), 7.03-6.94 (m, 2H) |

EXAMPLE 10

Effect of Copper on Activity of Hydrazones Towards *Chlamydomonas reinhardtii*

In vitro toxicity assays against *C. reinhardtii* CC-1928 (wild type mt+137c green in dark subclone) obtained from the Chlamydomonas Resource Center at Duke University were conducted using TAP liquid growth medium described by Gorman and Levine *Proc. Natl. Acad. Sci. USA* 1965, 54, 1665-1669 except that $CuSO_4.5H_2O$, normally included as a component of Hutner's trace element stock solution (Hutner et al. *Proc. Am. Philos. Soc.* 1950, 94, 152-170), was omitted. The TAP medium lacking Cu (TAP Cu minus) was prepared by adding 400 mg $NH_4Cl$, 10 mL of 100× Tris-Acetate (242 g Tris-base and 100 mL glacial acetic acid in 1000 mL milli Q water), and 8.3 mL of 120.5× phosphate buffer (14.34 g $K_2HPO_4$ and 7.26 g $KH_2PO_4$ in 1000 mL milli Q water) to milli Q water to make a total volume of 1 liter. The medium was treated with 0.5 g Chelex 100 resin (Bio-Rad Analytical grade, 50-100 mesh, sodium form, cat#142-2822) by stirring at room temperature for 1 hour. 900 mL were decanted and 45.9 mg of $CaCl_2.2H_2O$, 90 mg of $MgSO_4.7H_2O$ and 0.9 mL Hutner's trace elements lacking $CuSO_4.5H_2O$ were added and the solution was filter-sterilized. Medium containing copper (TAP Cu plus) was prepared by adding $CuCl_2.2H_2O$ to the TAP Cu minus medium at 20 μM. Test compounds were dissolved in dimethylsulfoxide (DMSO) at 2 mg/mL then dilutions in TAP Cu minus and TAP Cu plus media were prepared in sterilized microcentrifuge tubes at 2 μg/mL. 100 μL aliquots of diluted compound were dispensed into flat-bottomed 96-well microtiter plates.

*C. reinhardtii* was maintained under 12 h of light on TAP agar plates at 18° C. A loopful of cells was added to 50 mL of TAP Cu minus medium and the culture incubated with shaking at 200 rpm at 27° C. for 24 h. The culture (10 to 20 mL aliquot) was centrifuged in a bench centrifuge at 2000 rpm for 2 min. The resulting cell pellet was resuspended in 5 mL sterile milli Q water (which had been treated with Chelex 100 resin using 0.5 g resin per liter of water by stirring at room temperature for 1 h), and recentrifuged. The cells were resuspended in TAP Cu minus medium, and the suspension adjusted to $2\times10^5$ spores per mL. Microtiter plates containing compounds as described above were inoculated with 100 μL of this cell suspension and the plates incubated at 27° C. for 48 h before assessing algal growth by measuring light scattering in a NepheloStar plate-reader. Growth inhibition was determined by comparing growth in the presence of test compound with growth in control wells lacking test compound.

Results for growth inhibition by test compounds at 1 μg/mL in TAP Cu plus medium (% Inhn Plus Copper Observed) were compared with predicted values (% Inhn Plus Copper Predicted) that were calculated using the formula set forth by S. R. Colby in *Weeds* 1967, 15, 20-22 based on results obtained for the same compounds in TAP Cu minus medium (% Inhn Minus Copper Observed). Copper chloride alone caused a slight enhancement of growth based on comparison of growth in TAP Cu minus and TAP Cu plus media without any test compound across experiments. Data are presented in Table 3. Results illustrate that hydrazones and copper produce a synergistic algicidal effect towards *C. reinhardtii*.

TABLE 3

Growth Inhibition of *C. reinhardtii*

| Compound Number | % Inhn. Minus Copper Observed | % Inhn. Plus Copper Observed | % Inhn. Plus Copper Predicted |
| --- | --- | --- | --- |
| 1 | 16 | 96 | 6 |
| 2 | 10 | 95 | −1 |
| 3 | 25 | 62 | 16 |
| 4 | 12 | 92 | 2 |
| 5 | 26 | 95 | 17 |
| 6 | 13 | 98 | 3 |
| 7 | 29 | 94 | 20 |
| 8 | 15 | 92 | 5 |
| 9 | 7 | 90 | −3 |
| 10 | 24 | 93 | 15 |
| 11 | 31 | 96 | 22 |
| 12 | 4 | 96 | −7 |
| 13 | 17 | 96 | 7 |
| 14 | 6 | 97 | −5 |
| 15 | 11 | 97 | 1 |
| 16 | −3 | 95 | −15 |
| 17 | 32 | 83 | 24 |
| 18 | 13 | 95 | 3 |
| 19 | 12 | 52 | 2 |
| 20 | −6 | 94 | −19 |
| 21 | 6 | 94 | −5 |
| 22 | −14 | 96 | −27 |
| 23 | −37 | 89 | −53 |
| 24 | −2 | 90 | −14 |
| 25 | 33 | 95 | 26 |
| 26 | 5 | 94 | −6 |
| 27 | 30 | 96 | 21 |
| 28 | 12 | 97 | 2 |
| 29 | 16 | 96 | 7 |
| 30 | 29 | 92 | 20 |
| 31 | −1 | 88 | −13 |
| 32 | 21 | 97 | 12 |
| 33 | 21 | 97 | 11 |
| 34 | 8 | 97 | −2 |
| 35 | 9 | 97 | −1 |
| 36 | 7 | 96 | −4 |
| 37 | 12 | 97 | 1 |
| 38 | 15 | 94 | 5 |
| 39 | 8 | 91 | −3 |
| 40 | 22 | 96 | 12 |
| 41 | 28 | 96 | 19 |
| 42 | 10 | 96 | 0 |
| 43 | 9 | 93 | −2 |
| 44 | 11 | 94 | 0 |
| 45 | 9 | 96 | −2 |
| 46 | 0 | 92 | −12 |
| 47 | −5 | 77 | −18 |
| 48 | 18 | 92 | 8 |
| 49 | 33 | 93 | 25 |
| 50 | 6 | 97 | −5 |
| 51 | −13 | 96 | −26 |
| 52 | −4 | 88 | −16 |
| 53 | 8 | 88 | −3 |
| 54 | −8 | 75 | −21 |
| 55 | −3 | 97 | −15 |
| 56 | 11 | 97 | 0 |
| 57 | −11 | 95 | −24 |
| 58 | 3 | 93 | −8 |
| 59 | −6 | 92 | −19 |
| 60 | −50 | 89 | −68 |
| 61 | −56 | 94 | −75 |
| 62 | 0 | 95 | −12 |
| 63 | −18 | 93 | −32 |
| 64 | −5 | 97 | −18 |
| 65 | −5 | 97 | −18 |
| 66 | −4 | 97 | −17 |
| $CuCl_2$, 10 μM | −11.7 ± 6.0 | | |

EXAMPLE 11

Effect of Copper on Activity of Hydrazones Towards *Synechocystis*

In vitro toxicity assays against the cyanobacterium (blue-green alga) *Synechocystis* sp. strain 6803 were conducted using BG-11 medium except that copper micronutrient, normally included as $CuSO_4.5H_2O$, was omitted. The medium, termed BG-11 Cu minus, was prepared by dissolving 1.5 g $NaNO_3$, 40 mg $K_2HPO_4$, 6 mg citric acid, 1 mg $Na_2EDTA$ and 20 mg $Na_2CO_3$ in 1 liter of milli Q water and treating the solution with 0.5 g Chelex 100 resin (Bio-Rad Analytical grade, 50-100 mesh, sodium form, cat#142-2822) by stifling at room temperature for 1 h. 900 mL were decanted and 67.5 mg $MgSO_4.7H_2O$, 32.4 mg $CaCl_2.7H_2O$, 5.4 mg ferric ammonium citrate and 0.9 mL trace metal mix A5 without copper (2.86 g $H_3BO_3$, 1.81 g $MnCl_2.4H_2O$, 222 mg $ZnSO_4.7H_2O$, 390 mg $Na_2MoO_4.2H_2O$ and $Co(NO_3)_2.6H_2O$ in 1 L Milli Q water) was added. The pH was adjusted to 7.1 and the medium was filter-sterilized. Medium containing copper (BG-11 Cu plus) was prepared by adding $CuCl_2.2H_2O$ to the BG-11 Cu minus medium at 0.2 μM. Test compounds were dissolved in dimethylsulfoxide (DMSO) at 2 mg/mL then appropriate dilutions in BG-11 Cu minus and BG-11 Cu plus media were prepared in sterilized microcentrifuge tubes. 100 μL aliquots were dispensed into flat-bottomed 96-well microtiter plates.

*Synechocystis* was maintained under 24 h of light on BG-11 agar plates at 27° C. A loopful of cells was added to 50 mL of BG-11 Cu minus growth medium and the culture was incubated with shaking at 200 rpm at 27° C. for 24 h. The culture (10 to 20 mL aliquot) was centrifuged in a bench centrifuge at 2400 rpm for 2 min. The resulting cell pellet was resuspended in 5 mL sterile milli Q water (which had been treated with Chelex 100 resin using 0.5 g resin per liter of water by stirring at room temperature for 1 h), and recentrifuged. The cells were resuspended in BG-11 Cu minus medium, and the suspension adjusted to $4 \times 10^5$ spores per mL. Microtiter plates containing compounds as described above were inoculated with 100 μL of this cell suspension and the plates incubated at 27° C. for 72 h before assessing algal growth by measuring light scattering in a NepheloStar plate reader. Growth inhibition was determined by comparing growth in the presence of test compound with growth in control wells lacking test compound.

Results for growth inhibition by test compounds in BG-11 Cu plus medium (% Inhn Plus Copper Observed) were compared with predicted values (% Inhn Plus Copper Predicted) that were calculated using the formula set forth by S. R. Colby in *Weeds* 1967, 15, 20-22 based on-results obtained for the same compounds in BG-11 Cu minus medium (% Inhn Minus Copper Observed) and the inhibition attributed to copper chloride alone, as determined by comparing growth in copper-minus and copper-plus media without any test compound across experiments. Data are presented in Table 4. Results illustrate that hydrazones and copper produce a synergistic algicidal effect towards *Synechocystis*.

TABLE 4

Growth Inhibition of *Synechocystis*

| Compound Number | Test Concn. μg/mL | % Inhn. Minus Copper Observed | % Inhn. Plus Copper Observed | % Inhn. Plus Copper Predicted |
| --- | --- | --- | --- | --- |
| 1 | 0.05 | 29 | 91 | 34 |
| 2 | 0.05 | −8 | 97 | −1 |
| 3 | 0.05 | −17 | 96 | −9 |

TABLE 4-continued

Growth Inhibition of Synechocystis

| Compound Number | Test Concn. µg/mL | % Inhn. Minus Copper Observed | % Inhn. Plus Copper Observed | % Inhn. Plus Copper Predicted |
|---|---|---|---|---|
| 4 | 0.05 | −14 | 96 | −6 |
| 5 | 0.05 | −10 | 91 | −2 |
| 6 | 0.05 | 19 | 99 | 25 |
| 7 | 0.05 | 22 | 96 | 28 |
| 8 | 0.05 | 62 | 92 | 65 |
| 9 | 0.00625 | 15 | 74 | 21 |
| 10 | 0.05 | 44 | 95 | 48 |
| 11 | 0.05 | 50 | 97 | 54 |
| 12 | 0.0125 | 21 | 82 | 27 |
| 13 | 0.05 | 22 | 96 | 28 |
| 14 | 0.05 | 50 | 97 | 54 |
| 15 | 0.00625 | 15 | 74 | 21 |
| 16 | 0.05 | −5 | 94 | 3 |
| 17 | 0.00625 | 59 | 72 | 62 |
| 18 | 0.0125 | 47 | 86 | 51 |
| 19 | 0.05 | −18 | 43 | −9 |
| 20 | 0.05 | 9 | 86 | 15 |
| 21 | 0.0125 | 39 | 96 | 43 |
| 22 | 0.05 | 48 | 94 | 52 |
| 23 | 0.0125 | 27 | 92 | 32 |
| 24 | 0.05 | 45 | 93 | 49 |
| 25 | 0.05 | 18 | 92 | 23 |
| 26 | 0.05 | 54 | 95 | 57 |
| 27 | 0.05 | 31 | 95 | 36 |
| 28 | 0.05 | 13 | 96 | 19 |
| 29 | 0.05 | 11 | 96 | 18 |
| 30 | 0.05 | 0 | 92 | 7 |
| 31 | 0.05 | 38 | 92 | 42 |
| 32 | 0.05 | 26 | 91 | 31 |
| 33 | 0.05 | 29 | 97 | 34 |
| 34 | 0.05 | 34 | 91 | 39 |
| 35 | 0.05 | 26 | 91 | 31 |
| 36 | 0.0125 | 28 | 87 | 33 |
| 37 | 0.0125 | 44 | 88 | 48 |
| 38 | 0.05 | 49 | 93 | 53 |
| 39 | 0.05 | 31 | 92 | 36 |
| 40 | 0.00625 | 4 | 64 | 11 |
| 41 | 0.0125 | 26 | 93 | 31 |
| 42 | 0.05 | 10 | 94 | 16 |
| 43 | 0.05 | 23 | 95 | 28 |
| 44 | 0.05 | 61 | 93 | 63 |
| 45 | 0.00625 | 33 | 78 | 38 |
| 46 | 0.0125 | 37 | 80 | 41 |
| 47 | 0.0125 | 24 | 60 | 29 |
| 48 | 0.05 | 32 | 95 | 37 |
| 50 | 0.05 | −7 | 95 | 0 |
| 51 | 0.05 | 17 | 97 | 23 |
| 52 | 0.0125 | 8 | 90 | 14 |
| 53 | 0.05 | 45 | 94 | 49 |
| 54 | 0.05 | 37 | 88 | 41 |
| 55 | 0.05 | 68 | 92 | 71 |
| 56 | 0.0125 | 28 | 75 | 33 |
| 57 | 0.05 | 61 | 92 | 64 |
| 58 | 0.025 | 46 | 64 | 50 |
| 59 | 0.05 | 1 | 93 | 8 |
| 60 | 0.0125 | 33 | 50 | 38 |
| 61 | 0.05 | 61 | 96 | 63 |
| 62 | 0.05 | 60 | 95 | 63 |
| 63 | 0.05 | 37 | 94 | 42 |
| $CuCl_2$, 10 µM | | 7.0 ± 4.6 | | |

EXAMPLE 12

Comparative Activity of Isolated Metal-Hydrazone Complexes and Parent Hydrazones Towards *Chlamydomonas Reinhardtii* and *Synechocystis*

Hydrazones and their isolated metal complexes were compared with respect to their in vitro activity toward *C. reinhardtii* and the cyanobacterium (blue-green alga) *Synechocystis* sp. strain 6803. Metal complexes of hydrazones were prepared by precipitation from ethanol with various metal salts at 1:1, 2:1 or 3:1 molar ratios, as described in general by Ainscough, Brodie, Dobbs, Ranford, and Waters (*Inorganica Chimica Acta* 1998, 267, 27-38, which is expressly incorporated by reference herein).

A general synthesis of 1:1 metal-hydrazone complexes is as follows. The starting salicylaldehyde benzoylhydrazone or 2-hydroxyphenylketone benzoylhydrazone is dissolved (or suspended) in EtOH (generally 0.1 mmol hydrazone per mL solvent) and agitated at a temperature ranging from room temperature to 80° C. for 30 min. To this solution (or suspension) is added 1 equivalent of the metal salt (generally as a 1 M solution in EtOH). The mixture is agitated for a period ranging from 1 to 24 h at a temperature ranging from room temperature to 80° C. The metal-hydrazone complex generally precipitates during the reaction or upon cooling and is isolated by filtration, washed with EtOH and finally washed with $Et_2O$. In the instances where the complex does not precipitate, the solvent is removed and the resulting solid metal-hydrazone complex is washed with $Et_2O$. Properties of particular metal complexes of hydrazones have been described (PCT Patent Application PCT/US10/021,040 filed on 14 Jan. 2010).

TABLE 5

Analytical Data for Complexes

| Complex Number | Parent Hydrazone Compound Number | Metal Salt | Ratio* | Appearance | mp (° C.) |
|---|---|---|---|---|---|
| 72 | 1 | $Cu(OCOCH_3)_2 \cdot H_2O$ | 1:1 | dark green solid | |
| 73 | 1 | $Cu(OCOCH_3)_2 \cdot H_2O$ | 2:1 | tan solid | 310-312 |
| 74 | 1 | $CuSO_4 \cdot 5H_2O$ | 2:1 | dark green solid | 310-312 |
| 75 | 1 | $CuCl_2 \cdot 2H_2O$ | 1:1 | light green olive solid | 311-312 |
| 76 | 1 | $CuCl_2 \cdot 2H_2O$ | 2:1 | light green solid | 288-290 |
| 77 | 1 | $MnCl_2 \cdot 4H_2O$ | 2:1 | mustard-colored solid | 250 |

TABLE 5-continued

Analytical Data for Complexes

| Complex Number | Parent Hydrazone Compound Number | Metal Salt | Ratio* | Appearance | mp (° C.) |
|---|---|---|---|---|---|
| 78 | 1 | $ZnCl_2$ | 2:1 | yellow-green solid | 250 |
| 79 | 7 | $CuCl_2 \cdot 2H_2O$ | 1:1 | olive green solid | 298-299 |
| 80 | 6 | $CuCl_2 \cdot 2H_2O$ | 1:1 | olive green solid | 215-219 |
| 81 | 63 | $CuCl_2 \cdot 2H_2O$ | 1:1 | olive green solid | 273-274 |
| 82 | 63 | $FeCl_3 \cdot 6H_2O$ | 1:1 | brown black solid | 199-202 |
| 83 | 63 | $FeCl_3 \cdot 6H_2O$ | 2:1 | dark green solid | 258-260 |
| 84 | 63 | $FeCl_3 \cdot 6H_2O$ | 3:1 | dark brown solid | 264-268 |
| 85 | 12 | $CuCl_2 \cdot 2H_2O$ | 1:1 | olive green solid | 242-247 |
| 86 | 14 | $CuCl_2 \cdot 2H_2O$ | 1:1 | olive green solid | 283-294 |
| 87 | 15 | $CuCl_2 \cdot 2H_2O$ | 1:1 | olive green solid | 224-235 |
| 88 | 14 | $CuCl_2 \cdot 2H_2O$ | 1:1 | olive green solid | 287-289 |
| 89 | 21 | $CuCl_2 \cdot 2H_2O$ | 1:1 | olive green solid | 299-308 |
| 90 | 25 | $CuCl_2 \cdot 2H_2O$ | 1:1 | olive green solid | 242-246 |
| 91 | 27 | $CuCl_2 \cdot 2H_2O$ | 1:1 | olive green solid | 280-286 |
| 92 | 32 | $CuCl_2 \cdot 2H_2O$ | 1:1 | olive green solid | 279-281 |
| 93 | 45 | $CuCl_2 \cdot 2H_2O$ | 1:1 | olive green solid | 257-267 |
| 94 | 52 | $CuCl_2 \cdot 2H_2O$ | 1:1 | olive green solid | 212-270 |
| 95 | 56 | $CuCl_2 \cdot 2H_2O$ | 1:1 | olive green solid | 270-274 |
| 96 | 64 | $CuCl_2 \cdot 2H_2O$ | 1:1 | olive green solid | 226-228 |
| 97 | 65 | $CuCl_2 \cdot 2H_2O$ | 1:1 | olive green solid | 245-248 |
| 98 | 66 | $CuCl_2 \cdot 2H_2O$ | 1:1 | olive green solid | 279-281 |
| 99 | 68 | $CuCl_2 \cdot 2H_2O$ | 1:1 | green solid | 206-289 |
| 100 | 26 | $CuCl_2 \cdot 2H_2O$ | 1:1 | olive green solid | 236-239 |

*Molar ratio of hydrazone:metal used to prepare complexes.

In vitro assays against *C. reinhardtii* were conducted as described in Example 10 using TAP Cu minus medium. Growth inhibition was determined by comparing growth in the presence of test compound with growth in control wells lacking test compound.

Results for growth inhibition of *C. reinhardtii* by hydrazones and corresponding isolated metal complexes (each at 1 μg/mL) are shown in Table 6. The results illustrate that isolated copper complexes of hydrazones have much higher activity against *C. reinhardtii* than the corresponding hydrazones and also are much more active than isolated Fe, Mn and Zn complexes of hydrazones.

TABLE 6

Growth Inhibition of *C. reinhardtii* by hydrazones and isolated metal-hydrazone complexes

| Parent Hydrazone Compound Number | Complex Number | Metal Salt | Ratio* | Hydrazone % Inhn. | Complex % Inhn. |
|---|---|---|---|---|---|
| 1 | 72 | $Cu(OCOCH_3)_2 \cdot H_2O$ | 1:1 | 16 | 96 |
| 1 | 73 | $Cu(OCOCH_3)_2 \cdot H_2O$ | 2:1 | 16 | 96 |
| 1 | 74 | $CuSO_4 \cdot 5H_2O$ | 2:1 | 16 | 96 |
| 1 | 75 | $CuCl_2 \cdot 2H_2O$ | 1:1 | 16 | 95 |

TABLE 6-continued

Growth Inhibition of C. reinhardtii by hydrazones and isolated metal-hydrazone complexes

| Parent Hydrazone Compound Number | Complex Number | Metal Salt | Ratio* | Hydrazone % Inhn. | Complex % Inhn. |
|---|---|---|---|---|---|
| 1 | 76 | $CuCl_2 \cdot 2H_2O$ | 2:1 | 16 | 75 |
| 1 | 77 | $MnCl_2 \cdot 4H_2O$ | 2:1 | 16 | −1 |
| 1 | 78 | $ZnCl_2$ | 2:1 | 16 | −5 |
| 7 | 79 | $CuCl_2 \cdot 2H_2O$ | 1:1 | 29 | 74 |
| 6 | 80 | $CuCl_2 \cdot 2H_2O$ | 1:1 | 13 | 72 |
| 63 | 81 | $CuCl_2 \cdot 2H_2O$ | 1:1 | −18 | 68 |
| 63 | 82 | $FeCl_3 \cdot 6H_2O$ | 1:1 | −18 | 23 |
| 63 | 83 | $FeCl_3 \cdot 6H_2O$ | 2:1 | −18 | 0 |
| 63 | 84 | $FeCl_3 \cdot 6H_2O$ | 3:1 | −18 | −4 |
| 12 | 85 | $CuCl_2 \cdot 2H_2O$ | 1:1 | 4 | 52 |
| 14 | 86 | $CuCl_2 \cdot 2H_2O$ | 1:1 | 6 | 74 |
| 15 | 87 | $CuCl_2 \cdot 2H_2O$ | 1:1 | 11 | 73 |
| 18 | 88 | $CuCl_2 \cdot 2H_2O$ | 1:1 | 13 | 47 |
| 21 | 89 | $CuCl_2 \cdot 2H_2O$ | 1:1 | 6 | 71 |
| 25 | 90 | $CuCl_2 \cdot 2H_2O$ | 1:1 | 33 | 49 |
| 27 | 91 | $CuCl_2 \cdot 2H_2O$ | 1:1 | 30 | 94 |
| 32 | 92 | $CuCl_2 \cdot 2H_2O$ | 1:1 | 21 | 95 |
| 45 | 93 | $CuCl_2 \cdot 2H_2O$ | 1:1 | 9 | 95 |
| 52 | 94 | $CuCl_2 \cdot 2H_2O$ | 1:1 | −4 | 96 |
| 56 | 95 | $CuCl_2 \cdot 2H_2O$ | 1:1 | 11 | 95 |
| 64 | 96 | $CuCl_2 \cdot 2H_2O$ | 1:1 | −5 | 95 |
| 65 | 97 | $CuCl_2 \cdot 2H_2O$ | 1:1 | −5 | 95 |
| 66 | 98 | $CuCl_2 \cdot 2H_2O$ | 1:1 | −4 | 95 |

*Molar ratio of hydrazone:metal used to prepare complexes.

In vitro assays against *Synechocystis* were conducted as described in Example 11 using BG-11 Cu minus medium. Growth inhibition was determined by comparing growth in the presence of test compound with growth in control wells lacking test compound.

Results for growth inhibition of *Synechocystis* by hydrazones and corresponding isolated metal complexes are shown in Table 7. The results illustrate that isolated copper complexes of hydrazones have much higher activity against *Synechocystis* than the corresponding hydrazones and also are much more active than isolated Fe, Mn and Zn complexes of hydrazones.

TABLE 7

Growth Inhibition of *Synechocystis* by hydrazones and isolated metal-hydrazone complexes

| Parent Hydrazone Compound Number | Complex Number | Metal Salt | Ratio* | Test Concn. µg/ml | Hydrazone % Inhn. | Complex % Inhn. |
|---|---|---|---|---|---|---|
| 1 | 72 | $Cu(OCOCH_3)_2 \cdot H_2O$ | 1:1 | 0.05 | 35 | 98 |
| 1 | 73 | $Cu(OCOCH_3)_2 \cdot H_2O$ | 2:1 | 0.05 | 35 | 97 |
| 1 | 74 | $CuSO_4 \cdot 5H_2O$ | 2:1 | 0.05 | 35 | 95 |
| 1 | 75 | $CuCl_2 \cdot 2H_2O$ | 1:1 | 0.05 | 35 | 97 |
| 1 | 76 | $CuCl_2 \cdot 2H_2O$ | 2:1 | 0.05 | 35 | 96 |
| 1 | 77 | $MnCl_2 \cdot 4H_2O$ | 2:1 | 0.05 | 35 | 35 |
| 1 | 78 | $ZnCl_2$ | 2:1 | 0.05 | 35 | 59 |
| 7 | 79 | $CuCl_2 \cdot 2H_2O$ | 1:1 | 0.0125 | 62 | 85 |
| 6 | 80 | $CuCl_2 \cdot 2H_2O$ | 1:1 | 0.025 | 70 | 91 |
| 63 | 81 | $CuCl_2 \cdot 2H_2O$ | 1:1 | 0.05 | 23 | 96 |
| 63 | 82 | $FeCl_3 \cdot 6H_2O$ | 1:1 | 0.05 | 23 | 24 |
| 63 | 83 | $FeCl_3 \cdot 6H_2O$ | 2:1 | 0.05 | 23 | 45 |
| 63 | 84 | $FeCl_3 \cdot 6H_2O$ | 3:1 | 0.05 | 23 | 33 |
| 27 | 91 | $CuCl_2 \cdot 2H_2O$ | 1:1 | 0.05 | 41 | 95 |
| 32 | 92 | $CuCl_2 \cdot 2H_2O$ | 1:1 | 0.05 | 68 | 95 |
| 52 | 94 | $CuCl_2 \cdot 2H_2O$ | 1:1 | 0.05 | 45 | 96 |
| 68 | 99 | $CuCl_2 \cdot 2H_2O$ | 1:1 | 0.05 | 16 | 94 |
| 26 | 100 | $CuCl_2 \cdot 2H_2O$ | 1:1 | 0.05 | 50 | 91 |

*Molar ratio of hydrazone:metal used to prepare complexes.

EXAMPLE 13

Effect of Copper on Activity of Metal-Hydrazone Complexes Towards Chlamydomonas Reinhardtii The effect of copper on activity of metal-hydrazone complexes towards *C. reinhardtii* was evaluated by comparing their activity in TAP Cu minus and TAP Cu plus media as described in Example 10 (compound concentrations were selected which gave low inhibition in TAP Cu minus medium). Growth inhibition was determined by comparing growth in the presence of test compound with growth in control wells lacking test compound.

Results for growth inhibition by test compounds in TAP Cu plus medium (% Inhn Plus Copper Observed) were compared with predicted values (% Inhn Plus Copper Predicted) that were calculated using the formula set forth by S. R. Colby in *Weeds* 1967, 15, 20-22 based on results obtained for the same compounds in TAP Cu minus medium (% Inhn Minus Copper Observed) and the inhibition attributed to copper chloride alone, as determined by comparing growth in TAP Cu minus and TAP Cu plus media without any test compound across experiments. Data are presented in Table 8. Results show that algicidal activity of metal complexes of hydrazones towards *C. reinhardtii* is synergistically enhanced in the presence of added copper. Furthermore, the fungitoxicity of copper complexes of hydrazones is synergistically enhanced in the presence of added copper.

TABLE 8

Growth Inhibition of *C. reinhardtii*

| Parent Hydrazone Compound Number | Complex Number | Metal Salt | Ratio* | Test Concn. μg/mL | % Inhn. Minus Copper Observed | % Inhn. Plus Copper Observed | % Inhn. Plus Copper Predicted |
|---|---|---|---|---|---|---|---|
| 1 | 72 | $Cu(OCOCH_3)_2 \cdot H_2O$ | 1:1 | 0.25 | 79 | 83 | 66 |
| 1 | 73 | $Cu(OCOCH_3)_2 \cdot H_2O$ | 2:1 | 0.25 | 23 | 87 | 10 |
| 1 | 74 | $CuSO_4 \cdot 5H_2O$ | 2:1 | 0.25 | −9 | 82 | −22 |
| 1 | 76 | $CuCl_2 \cdot 2H_2O$ | 2:1 | 0.5 | 3 | 89 | −10 |
| 1 | 75 | $CuCl_2 \cdot 2H_2O$ | 1:1 | 0.25 | 18 | 59 | 5 |
| 63 | 82 | $FeCl_3 \cdot 6H_2O$ | 1:1 | 0.5 | −16 | 89 | −29 |
| 63 | 83 | $FeCl_3 \cdot 6H_2O$ | 2:1 | 0.5 | −2 | 58 | −15 |
| 63 | 84 | $FeCl_3 \cdot 6H_2O$ | 3:1 | 0.5 | −19 | 70 | −32 |
| 1 | 77 | $MnCl_2 \cdot 4H_2O$ | 2:1 | 0.5 | −5 | 93 | −18 |
| 1 | 78 | $ZnCl_2$ | 2:1 | 0.5 | −9 | 87 | −22 |
| $CuCl_2$, 10 μM | | | | | −12.9 | | |

*Molar ratio of hydrazone:metal used to prepare complexes.

The invention claimed is:

1. A mixture effective in controlling the growth of algae, the mixture including copper and a hydrazone compound of Formula 1:

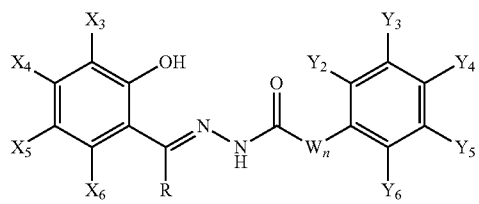

Formula 1 wherein W is —CHR1-;

n is 0 or 1;

R is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, or $C_3$-$C_6$ halocycloalkyl;

R1 is H, $C_1$-$C_6$ alkyl, $C_2$-$C_6$ alkenyl, and $C_2$-$C_6$ alkynyl;

$X_3$, $X_4$, $X_5$, and $X_6$ are each independently selected from the group consisting of H, halogen, nitro, hydroxyl, cyano, $C_1$-$C_4$ alkyl, $C_1$-$C_4$ alkoxy, $C_2$-$C_4$ alkenyl, $C_2$-$C_4$ alkynyl, $C_1$-$C_4$ alkylthio, $C_1$-$C_4$ haloalkyl, $C_1$-$C_4$ haloalkoxy, $C_2$-$C_4$ haloalkenyl, $C_2$-$C_4$ haloalkynyl, $C_1$-$C_4$ haloalkylthio, —$SO_2$R1, —SONR1R1, —CR1=NOR1, —CONR1R1, —NR1COOR1, and —COOR1; and $Y_2$, $Y_3$, $Y_4$, $Y_5$, and $Y_6$ are each independently selected from the group consisting of H, halogen, nitro, hydroxyl, cyano, $C_1$-$C_4$ alkyl, $C_1$-$C_4$ alkoxy, $C_2$-$C_4$ alkenyl, $C_2$-$C_4$ alkynyl, $C_1$-$C_4$ alkylthio, $C_1$-$C_4$ halo alkyl, $C_1$-$C_4$ haloalkoxy, $C_2$-$C_4$ haloalkenyl, $C_2$-$C_4$ haloalkynyl, $C_1$-$C_4$ haloalkylthio, —$SO_2$R1, —SONR1R1, —R1=NOR1, —CONR1R1, —NR1COOR1, —COOR1, and —NR1R1;

with the proviso that when $Y_2$ is a hydoxyl group, then $X_3$, $X_4$, $X_5$ and $X_6$ are not all H, wherein the copper and the hydrazine compound are present in a ratio such that the mixtures exhibit synergistic algicidal activity.

2. The mixture according to claim 1, wherein the mixture exhibits synergistic activity against algae selected from the group consisting of *Chlamydomonas reinhardtii*, *Chlorella pyrenoidosa*, *Scenedesmus quadricauda*, *Chlorococcum oleofaciens*, *Selenastrum* species, *Phormidium* species, *Anabaena flosaquae*, *Nostoc commune*, *Osiffiatorae* species, *Synechocystis* species, *Synechococcus* species; and *Dunaliella parva*.

3. The mixture according to claim 1, wherein the total molar ratio of copper to the hydrazone compound of Formula 1 exceeds 1:1.

4. The mixture according to claim 1, wherein the total molar ratio of the copper to the hydrazone compound of Formula 1 is from 1:1 to 1:2.

5. The mixture of claim 1, wherein the hydrazone compound of Formula 1 to be combined with copper is complexed with a metal.

6. The mixture of claim 5, wherein the metal complexed with the hydrazone compound of Formula 1 is selected from the group consisting essentially of $Cu^+$, $Cu^{2+}$, $Fe^{2+}$, $Fe^{3+}$, $Zn^{2+}$, and $Mn^{2+}$.

7. The mixture of claim 1, wherein the copper in the mixture is selected from the group consisting of: copper oxychloride, copper octanoate, copper ammonium carbonate, copper arsenate, copper oxysulfate, copper formate, copper propionate, copper oxyacetate, copper citrate, copper chloride, copper diammonium chloride, copper nitrate, copper carbonate, copper phosphate, copper pyrophosphate, copper dis odium EDTA, copper diammonium EDTA, copper oxalate, copper tartrate, copper gluconate, copper glycinate, copper glutamate, copper aspartate, copper adipate, copper palmitate, copper stearate, copper caprylate, copper decanoate, copper undecylenate, copper neodecanoate, copper linoleate, copper oleate, copper borate, copper methanesulfonate, copper sulfamate, copper acetate, copper hydroxide, copper oxide, copper oxychloride-sulfate, copper sulfate, basic copper sulfate, copper-oxine, copper 3-phenylsalicylate, copper chloride hydroxide, copper dimethyldithiocarbamate, ammonium copper sulfate, copper magnesium sulfate, copper naphthenate, copper ethanolamine, chromated copper arsenate, ammoniacal copper arsenate, ammoniacal copper zinc arsenate, ammoniacal copper borate, Bordeaux mixture, copper zinc chromate, cufraneb, cupric hydrazinium sulfate, cuprobam, nano-copper materials, copper didecyldimethylammonium chloride, Algimycin P11-C, Aquatrine, A&V-70, Cutrine-plus, Stocktrine II and K-Tea algicide and where suitable the hydrates of said compounds.

8. The mixture of claim 1, wherein a ratio of the hydrazone compound of Formula 1 to the copper in the mixture is from 1:0.1 to 1:10,000.

9. The mixture of claim 1, wherein the hydrazone compound of Formula 1 is:

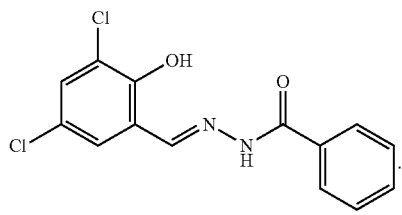 [SMILES: O=C(N/N=C/c1cc(Cl)cc(Cl)c1O)c1ccccc1]

10. An algicidal composition including the mixture of claim 1 and at least one of a fungicide, a herbicide, an insecticide, a bacteriocide, a nematocide, a miticide, a biocide, a termiticide, a rodenticide, a molluscide, an arthropodicide, a fertilizer, a growth regulator, and a pheromone.

11. A method for controlling the growth of algae, comprising the steps of
applying an algicidal effective amount of at least one of the mixtures of claim 1 to wood, metal or plastic.

12. The method according to claim 11, wherein the algae is selected from the group consisting of green algae and blue-green algae.

* * * * *